US008689798B2

(12) United States Patent
Sabin

(10) Patent No.: US 8,689,798 B2
(45) Date of Patent: Apr. 8, 2014

(54) PROTECTIVE MEDICAL DEVICE CUSHION AND METHOD FOR USE THEREOF

(76) Inventor: David C Sabin, Rougemont, NC (US)

( * ) Notice: Subject to any disclaimer, the term of this patent is extended or adjusted under 35 U.S.C. 154(b) by 663 days.

(21) Appl. No.: 12/796,786

(22) Filed: Jun. 9, 2010

(65) Prior Publication Data

US 2010/0307510 A1 Dec. 9, 2010

Related U.S. Application Data

(60) Provisional application No. 61/185,496, filed on Jun. 9, 2009.

(51) Int. Cl.
*A61F 5/37* (2006.01)
(52) U.S. Cl.
USPC .............................. 128/877; 604/174; 604/180
(58) Field of Classification Search
USPC ............................ 604/174, 179, 180; 128/877
See application file for complete search history.

(56) References Cited

U.S. PATENT DOCUMENTS

| 3,834,380 | A | * | 9/1974 | Boyd | 604/180 |
| 4,480,639 | A | * | 11/1984 | Peterson et al. | 128/207.18 |
| 5,069,206 | A | * | 12/1991 | Crosbie | 128/207.17 |
| 5,263,939 | A | * | 11/1993 | Wortrich | 604/174 |
| 5,643,217 | A | * | 7/1997 | Dobkin | 604/180 |
| 5,681,290 | A | * | 10/1997 | Alexander | 604/180 |
| 5,686,096 | A | * | 11/1997 | Khan et al. | 424/443 |
| 7,320,681 | B2 | * | 1/2008 | Gillis et al. | 604/174 |
| 2005/0027258 | A1 | * | 2/2005 | Bierman et al. | 604/174 |

* cited by examiner

*Primary Examiner* — Patricia Bianco
*Assistant Examiner* — Camtu Nguyen
(74) *Attorney, Agent, or Firm* — Taft Stettinius & Hollister, LLP; Anthony P. Filomena, Esq.

(57) ABSTRACT

A protective cushion for preventing a medical device from damaging the skin of a patient and a method for using the cushion. The cushion includes a bottom portion made of soft material and configured for resting against the patient's body and separating the medical device from the patient's body; and a top portion configured for receiving the medical device. The soft material can be resistant to bacterial growth. The bottom portion can have a concave curvature to fit against the patient's body. The top portion can include an opening shaped for receiving the medical device. The opening can separate the top portion into first and second side portions. The top portion can include a fastening system for securing the medical device in the protective cushion. The fastening system can include a tab or the opening shape. The cushion can include a cover for covering the opening in the top portion.

15 Claims, 4 Drawing Sheets

PROTECTIVE MEDICAL DEVICE CUSHION AND METHOD FOR USE THEREOF

This application claims priority to U.S. Provisional Patent Application Ser. No. 61/185,496, filed Jun. 9, 2009 entitled "Protective Medical Device Cushion," the disclosure of which is expressly incorporated herein by reference.

FIELD OF DISCLOSURE

The present disclosure relates generally to medical devices, and more particularly, to protective cushions to protect a patient from injury due to rigid medical devices against the skin.

BACKGROUND

Many modern surgical procedures require that the patient's extremities be tucked at their side to provide optimal surgical exposure. Many times, one or both of the patient's arms are placed directly at the patient's side. To insure that the patient's extremities do not move, they are cushioned and immobilized. It is the responsibility of all the members of the surgical team (operating room nurses, anesthesia, surgeon, etc.) to protect the patient from positioning injuries. Rigid devices, such as hard plastic patient access devices used with intravenous lines and arterial lines, can cause tissue or nerve compression injuries. These devices need to be padded so that they do not cause injuries to the patient.

To protect the patient during surgery, operating room personnel usually wrap the individual rigid devices with non-sterile gauze and tape. For example, the anesthesia staff may have to manually tape and pad any hard plastic components of the intravenous or arterial tubing such as access ports which are often directly adjacent to the patient's extremities. This creates a soft bundle which rests against the patient's body. When the extremities are immobilized it is often done with sheets or safety straps firmly placed against the patient. Utmost care is taken to insure that there is not direct contact between the rigid devices and the patient's skin.

When the surgery is complete, the padding process is reversed. This involves taking off the non-sterile gauze and tape on the rigid devices. Depending on the amount of tape around the devices, this can take several minutes when time is critical. The tape can also leave a sticky residue around the rigid devices and/or connective tubing. This sticky residue can be an attractant to germs. Although the type of positioning is necessary for a successful surgical outcome, the wrapping and unwrapping can be time consuming at especially critical times.

Thus, it would be desirable to have a method and device to protect the patient from injury due to rigid medical devices against the skin, and it would also be desirable for the method and device to allow for rapid application to and removal from the patient.

SUMMARY

A protective cushion having a soft flexible exterior can be placed around a rigid device, and can be removed quickly from the device to provide the desired patient protection and ease of use. The soft exterior protective cushion can reduce the concern of a tissue or nerve compression injury from happening during surgery. The protective cushion can also provide a constant standard of protection when positioning intravenous and arterial access devices. The soft flexible protective cushion can provide a constant standard of padding, and can be made of materials that do not support bacterial growth.

Placing an access port or other device in the protective cushion can provide coverage of the hard plastic or other rigid surfaces, preventing the rigid device from coming into contact with the skin of the patient. The protective cushion can be placed against the patient's skin and the rigid device placed within the protective cushion. The patient's extremities can then be firmly immobilized with sheets, safety straps or other immobilization apparatus without the need of wrapping or taping the individual ports. This reduces the time spent in preparation before and after surgery, and eliminates the need for tape and the sticky residue from the tape that can be left behind on the rigid device, the connective tubing or the patient's skin. When the surgery is finished, the protective cushion can simply be slid off to expose the access port for use.

An exemplary embodiment of a protective cushion for preventing a medical device from damaging the skin of a patient includes a bottom portion and a top portion. The bottom portion is made of a soft material and is configured for resting against the body of the patient and separating the medical device from the body of the patient. The top portion is configured for receiving the medical device. The top portion can also be made of the soft material. The soft material can be resistant to bacterial growth. A bottom face of the bottom portion can be shaped with a concave curvature to fit securely against the body of the patient. The top portion can have a tapered shape that is wider at a proximal end adjacent to the bottom portion and narrower at a distal end away from the bottom portion.

The top portion of this embodiment can include an opening shaped for receiving the medical device. The opening can extend across the length of the top portion to separate a first side portion from a second side portion. Either or both of the first and second side portions can have a narrower central portion and wider peripheral portions for receiving the medical device.

The top portion can include a fastening system for securing the medical device in the protective cushion. At least one of the first and second side portions can include a tab as part of the fastening system wherein, when the medical device is inserted into the opening, the tab prevents the medical device from falling out of the opening separating the first and second side portions. The first and second side portions can cooperatively form the fastening system. The opening separating the first and second side portions can be wider at a proximal end adjacent to the bottom portion and narrower at a distal end away from the bottom portion, such that, when the medical device is inserted into the opening, the narrower distal end prevents the medical device from falling out of the opening separating the first and second side portions. The width of the opening at the proximal end can be substantially equal to the outside diameter of the medical device and the width of the opening at the distal end can be less than the outside diameter of the medical device.

The protective cushion can also include a cover for covering the opening in the top portion. The opening in the top portion can separate the top portion into a plurality of separate side portions. The top portion can include a plurality of openings.

Another exemplary embodiment of a protective cushion for preventing a medical device from damaging the skin of a patient includes a bottom portion, a top portion and a fastening system. The bottom portion is configured for resting against the skin of the patient and separating the medical device from the body of the patient. The top portion includes a first side portion, a second side portion, and an opening separating the first side portion from the second side portion, the opening being shaped for receiving the medical device. The fastening system is configured for securing the medical device in the protective cushion such that, when the medical device is inserted into the opening of the top portion, the fastening system prevents the medical device from falling out of the opening. The protective cushion can be made of a soft material that resists bacterial growth.

A method for using a protective cushion to prevent a medical device from damaging the skin of a patient during a procedure is disclosed. The method includes, prior to starting the procedure, both placing the protective cushion between the medical device and the body of the patient; and immobilizing the protective cushion, the medical device and the body of the patient using immobilization apparatus. The method then includes, following the procedure, removing the immobilization apparatus, and removing the protective cushion. The step of placing the protective cushion between the medical device and the body of the patient can include inserting the medical device into an opening in the protective cushion. The step of placing the protective cushion can also include securing the medical device in a fastening system of the protective cushion that prevents the medical device from falling out of the opening; and the step of removing the protective cushion can include releasing the medical device from the fastening system of the protective cushion.

For a more complete understanding of the present disclosure, reference is now made to the following detailed description and the accompanying drawings.

DETAILED DESCRIPTION OF EXEMPLARY EMBODIMENTS

Figure 1:
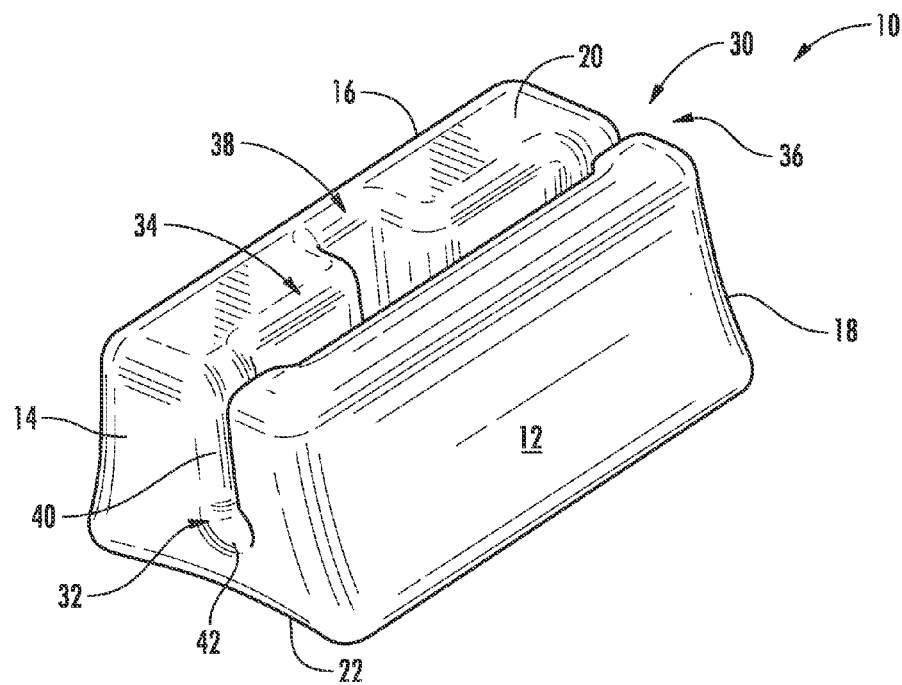
FIG. 1 shows a perspective view of an exemplary embodiment of a protective medical device cushion.
Figure 2:
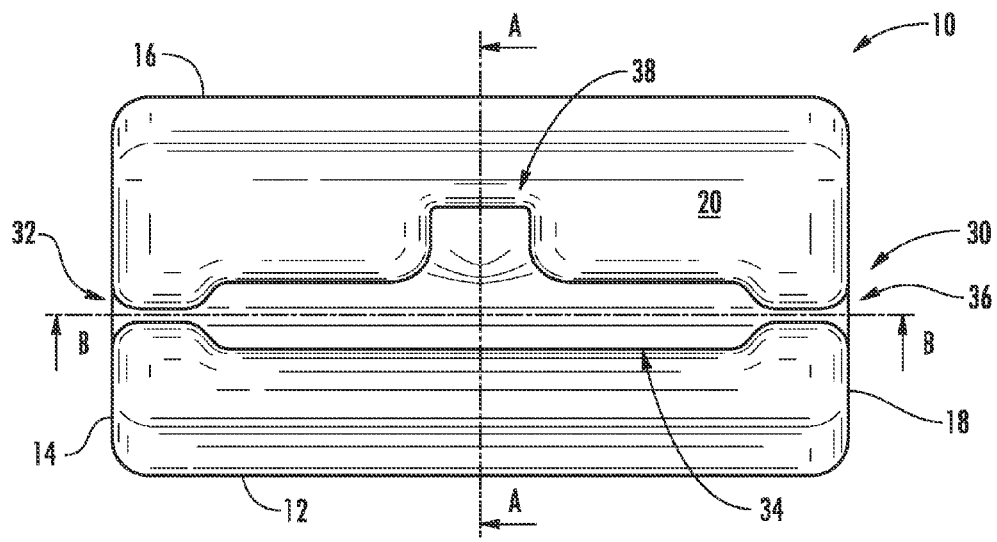
FIG. 2 shows a top view of a protective medical device cushion.
Figure 3:
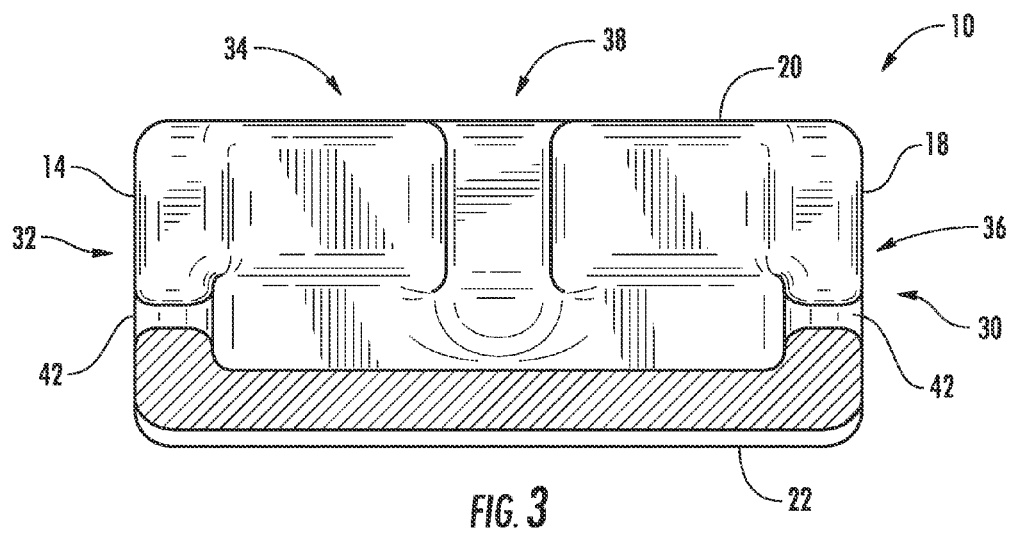
FIG. 3 shows a cross-section view of the protective medical device cushion of FIG. 2 along the line B-B.
Figure 4:
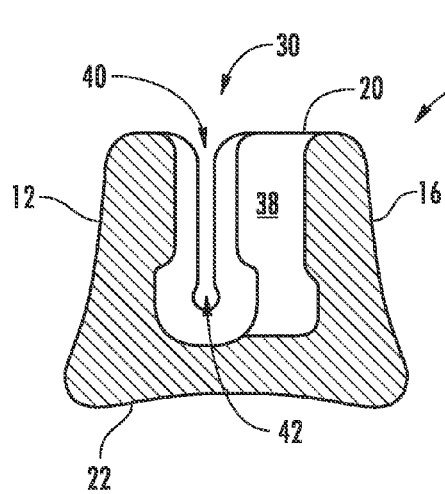
FIG. 4 shows a cross-section view of the protective medical device cushion of FIG. 2 along the line A-A.
Figure 5:
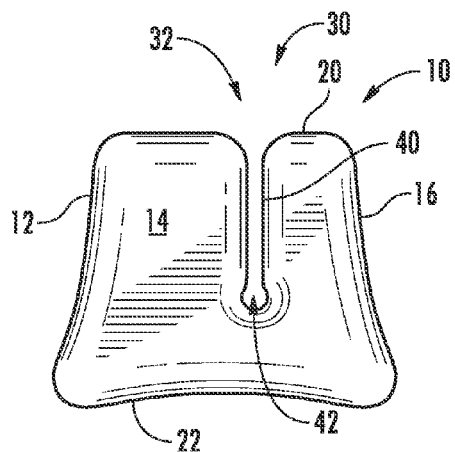
FIG. 5 shows a side view of a protective medical device cushion.
Figure 6:
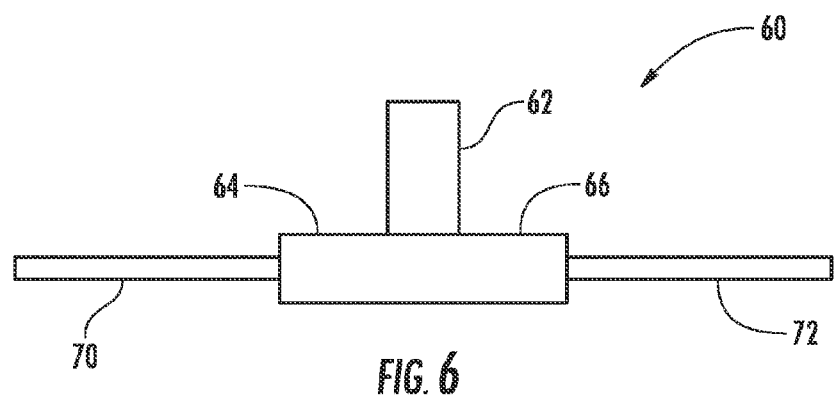
FIG. 6 shows an exemplary access port.

FIGS. 1-5 show an embodiment of a protective medical device cushion 10 that can be used for a hard plastic access port used with intravenous lines or arterial lines. The access port is typically coupled to a catheter using tubing. The catheter is typically transcutaneously implanted on the patient's body and then left in place for extended periods for repeated withdrawal or delivery of fluids from/to the patient's body. An exemplary access port 60 is shown in FIG. 6. The access port 60 includes a control arm 62, a fluid entry arm 64 and a fluid exit arm 66. The fluid entry arm 64 is connected to entry tubing 70, and the fluid exit arm 66 is connected to exit tubing 72. The control arm 62 controls the flow of fluid between the fluid entry arm 64 and the fluid exit arm 66.

This embodiment of the protective medical device cushion 10 comprises a flexible single piece having a front face 12, a left side face 14, a rear face 16, a right side face 18, a top face 20 and a bottom face 22. The protective medical device cushion 10 can have a soft flexible exterior surface or can be completely made out of a flexible material, such as foam. The protective cushion 10 can be made of materials that resist bacterial growth. The bottom face 22 is solid foam with no openings, and can be shaped with a concave curvature to fit securely against a patient's body. The front face 12 and the rear face 16 can be tapered from wider at a proximal end adjacent to the bottom face 22 to narrower at a distal end adjacent to the top face 20 to provide additional stability of the protective cushion 10 against the patient's body. The left side face 14 and the right side face 18 can also be tapered from wider at a proximal end adjacent to the bottom face 22 to narrower at a distal end adjacent to the top face 20 to further provide stability of the protective cushion 10 against the patient's body.

The protective cushion 10 has an opening 30 that extends from the left side face 14 to the right side face 18. The opening 30 separates a top portion of the protective cushion 10 into a first side portion that includes the front face 12 and a second side portion that includes the rear face 16. The opening 30 includes a left side opening 32 in the left side face 14, a right side opening 36 in the right side face 18 and a wider central latitudinal section 34 running between the left side opening 32 and the right side opening 36. The central latitudinal section 34 can also include a central longitudinal protrusion 38. The opening 30 is sized and shaped to fit the access port 60. The access port 60 can be inserted into the opening 30 such that the control arm 62, the fluid entry arm 64 and the fluid exit arm 66 fit into the central latitudinal section 34; the entry tubing 70 extends through the left side opening 32 and the exit tubing 72 extends through the right side opening 36. The central longitudinal protrusion 38 can be sized and shaped to accommodate the control arm 62 of an access port in which the control arm has a larger diameter or flow controls on the side of the control arm 62. Of course, the fluid flow can be in the opposite direction such that the exit tubing 72 extends through the left side opening 32 and the entry tubing 70 extends through the right side opening 36.

The left side opening 32 can include an upper slit section 40 having an upper width and a lower circular section 42 having a lower diameter. The lower diameter of the circular section 42 can be approximately equal to the outside diameter of the entry tubing 70 or the exit tubing 72, and the upper width of the upper slit section 40 can be smaller than the outside diameter of the entry tubing 70 or the exit tubing 72. In this case, placing the entry or exit tubing in the circular section 42 helps fasten the tubing 70, 72 and the access port 60 into the protective cushion 10. The right side opening 36 can be similarly shaped to also help fasten the entry/exit tubing 70, 72 and the access port 60 into the protective cushion 10.

An exemplary method of using the protective cushion 10 can include the following. When a procedure is to be performed that requires a patient's extremity to be wrapped against the patient's body, and a rigid device is attached to the patient such that it would be wrapped against the patient' skin, then a protective cushion can be used to prevent the rigid device from damaging the patient's skin. The protective cushion can be placed against the patient's body such that the rigid device does not come into contact with the patient's skin. The patient's extremity along with the protective cushion and rigid device can then be firmly immobilized with sheets, safety straps or other immobilization apparatus during the procedure. When the procedure is complete, the sheets, safety straps or other immobilization apparatus can be removed and the protective cushion can simply be slid off to expose the rigid device for use.

Figure 7:
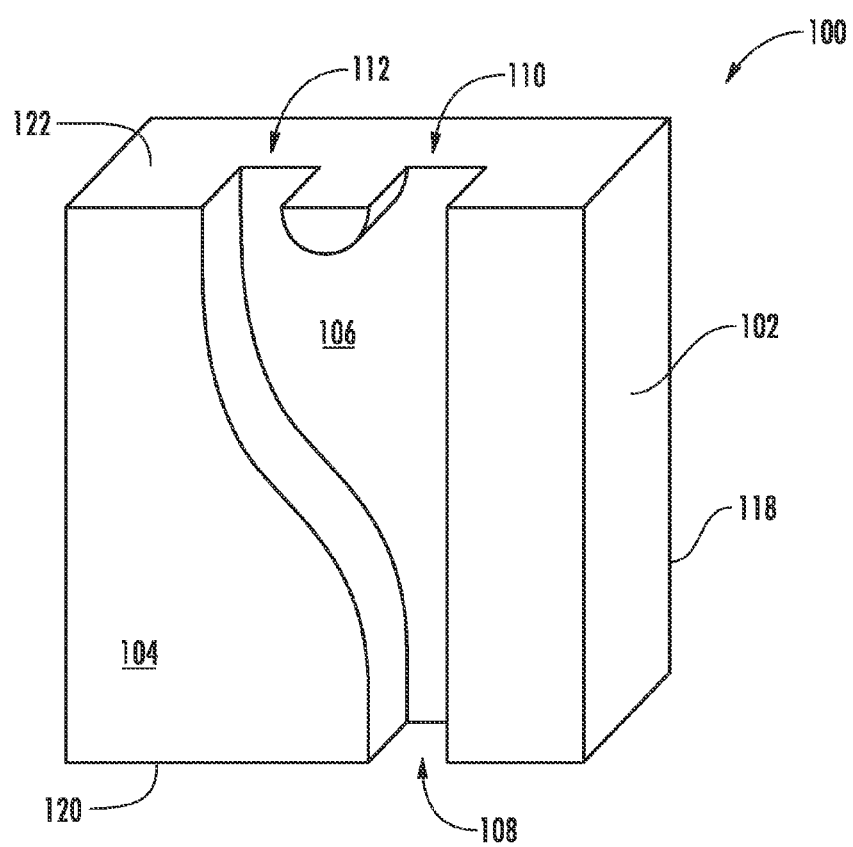
FIG. 7 shows a schematic of another embodiment of a protective medical device cushion.
Figure 8:
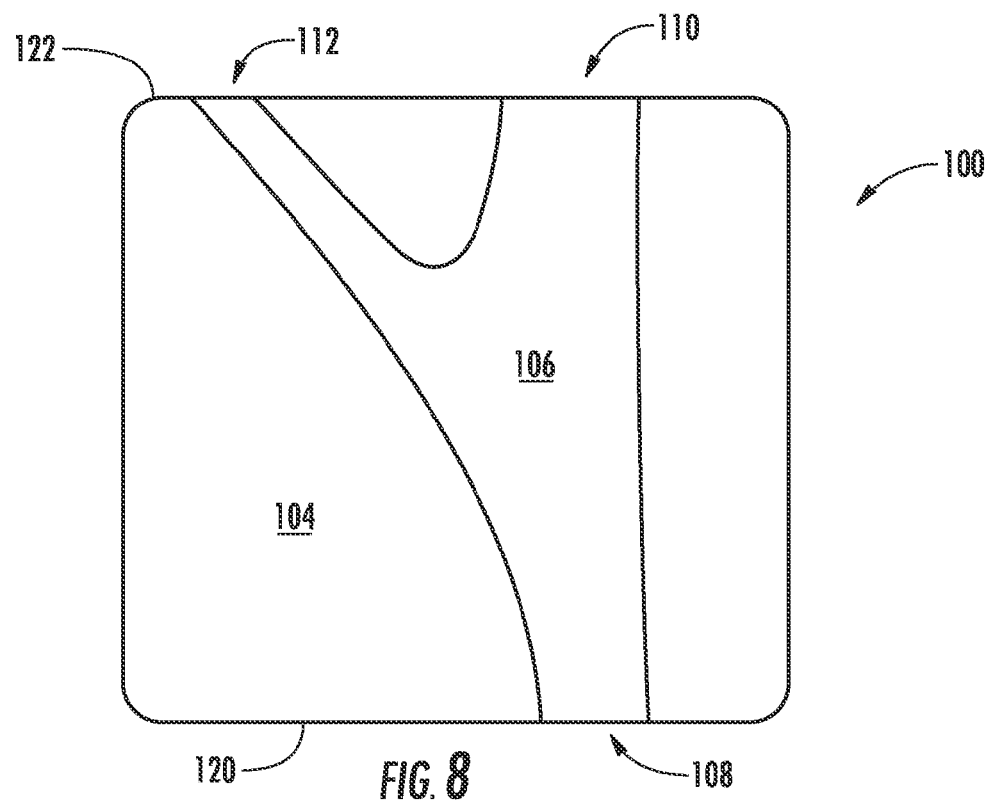
FIG. 8 shows a front view of an embodiment of a protective medical device cushion.
Figure 9:
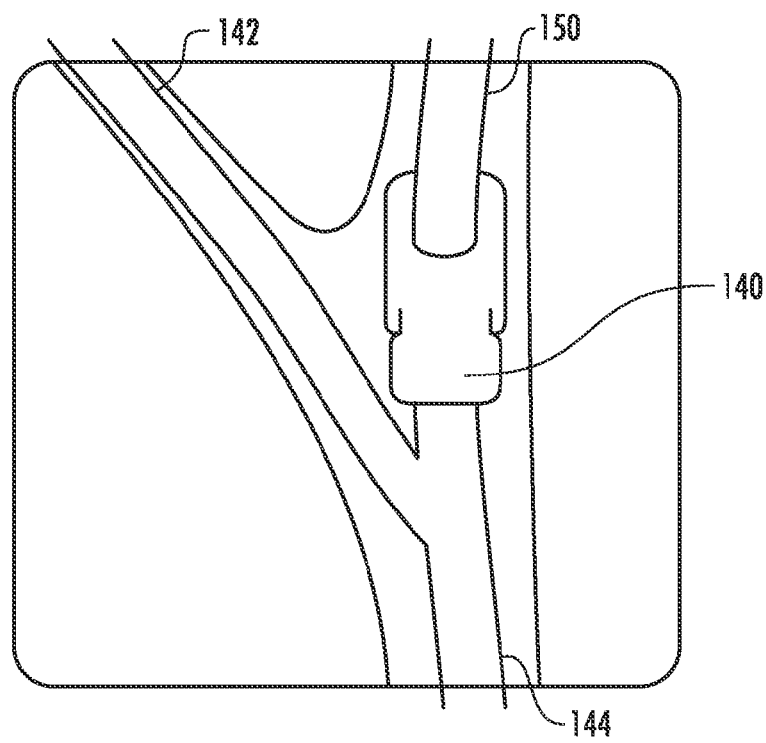
FIG. 9 shows a medical device in the embodiment of the protective medical device cushion shown in FIG. 8.

FIGS. 7-9 show another embodiment of a protective medical device cushion 100 that can be used for a hard plastic access port used with intravenous lines. FIG. 7 shows a schematic of the protective medical device cushion embodiment 100, and FIG. 8 shows a prototype of the protective medical device cushion embodiment 100. This embodiment of the protective cushion 100 comprises a flexible single piece 102 having a front face 104, a back face 118, a bottom face 120 and a top face 122. The protective medical device cushion 100 can have a soft flexible exterior surface or can be completely made out of a flexible material, such as foam. The protective cushion 100 can be made of materials that resist bacterial growth.

The protective cushion 100 has an opening 106 carved into the front face 104 that extends from the bottom face 120 to the top face 122. The opening 106 extends from a lower opening 108 at the bottom face 120 to a first upper opening 110 and a second upper opening 112 at the top face 122. FIGS. 7-9 show the entire opening 106 being open to front face 104 of the cushion 100. Alternatively, the cushion 100 could include a cover (not shown) that covers the opening 106 and/or the front face 104, or could include fastening mechanisms, such as tabs, (not shown) to hold a medical device (shown in FIG. 9) within the opening 106.

FIG. 9 shows another exemplary medical device, an intravenous line Luer lock device that could be used with the protective cushion 100. The exemplary medical device includes a Luer lock adapter 140 and an infusion or secondary line 150 connected to the Luer lock adapter 140. The Luer lock adapter 140 includes an entry line 142 and exit line 144. The Luer lock adapter 140 is positioned in the opening 106 of the cushion 100 such that the entry line 142 extends through the second upper opening 112 in the top face 122 and the exit line 144 extends through the lower opening 108 in the bottom face 120. The infusion line 150 connected to the Luer lock adapter 140 extends through the first upper opening 110 in the top face 122.

An exemplary method of using the protective cushion 100 can include the following. When a procedure is to be performed that requires a rigid device, such as the Luer lock device 140, that needs to be wrapped against a patient's body, the following steps can be performed. A protective cushion 100 can be obtained and the rigid device 140 placed in the opening 106 of the cushion 100 such that the entry and exit tubes pass through the openings 108, 110 and 112. The protective cushion is then placed against the patient's body such that the back face 118 is towards the patient's body and the front face 104 with the opening 106 and the rigid device 140 are facing away from the patient's body. An optional cover can be placed over the opening 106. Alternatively, an optional fastening system can be used to help fasten the Luer lock device 140 in the protective cushion 100. The patient's extremities along with the protective cushion 100 and rigid device 140 can then be firmly immobilized with sheets, safety straps or other immobilization apparatus during the procedure. When the procedure is complete, the sheets, safety straps or other immobilization apparatus can be removed and the rigid device 140 can be removed from the protective cushion 100.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

I claim:

1. A protective cushion for preventing a medical device from damaging the skin of a patient, the protective cushion comprising:
   a flexible single piece made of a soft material, the flexible single piece comprising:
   a bottom portion for resting against the skin of the patient and separating the medical device from the skin of the patient; and
   a top portion having an opening shaped for receiving the medical device, the opening extending across the length of the top portion and separating a first side portion from a second side portion, wherein the first side portion comprises a narrower central portion and two wider peripheral portions on opposite ends of the narrower central portion making the opening wider adjacent to the narrower central portion and making the opening narrower adjacent to the wider peripheral portions;
   wherein the top portion includes a fastening system for securing the medical device in the protective cushion, the first and second side portions cooperatively forming the fastening system; and wherein the opening is wider at a proximal end adjacent to the bottom portion and narrower at a distal end away from the bottom portion, such that, when the medical device is inserted into the opening, the narrower distal end of the opening prevents the medical device from falling out of the opening.

2. The protective cushion of claim 1, wherein at least one of the first and second side portions is shaped such that the opening separating the first and second side portions is wider at the proximal end adjacent to the bottom portion and narrower at the distal end away from the bottom portion wherein, when the medical device is inserted into the opening, the shape of the at least one of the first and second side portions helps prevent the medical device from falling out of the opening separating the first and second side portions.

3. The protective cushion of claim 1, wherein the soft material is designed to resist bacterial growth.

4. The protective cushion of claim 1, wherein a bottom face of the bottom portion is shaped with a concave curvature.

5. The protective cushion of claim 1, wherein the top portion has a tapered shape that is wider at the proximal end adjacent to the bottom portion and narrower at the distal end away from the bottom portion.

6. The protective cushion of claim 1, wherein the width of the opening at the proximal end is substantially equal to the outside diameter of a portion of the medical device and the width of the opening at the distal end is less than the outside diameter of that portion of the medical device.

7. The protective cushion of claim 1, wherein the narrower central portion of the first side portion includes a central longitudinal protrusion for receiving at least a portion of the medical device.

8. A protective cushion for preventing a medical device from damaging the skin of a patient, the protective cushion comprising:
   a bottom portion for resting against the skin of the patient and separating the medical device from the skin of the patient;

a top portion configured for receiving the medical device, the top portion including an opening shaped for receiving the medical device, the opening extending across the length of the top portion and separating a first side portion from a second side portion, the first side portion comprising a narrower central portion and two wider peripheral portions on opposite ends of the narrower central portion and the second side portion comprising a narrower central portion and two wider peripheral portions on opposite ends of the narrower central portion making the opening wider between the narrower central portions of the first and second side portions and making the opening narrower between to the wider peripheral portions of the first and second side portions;

wherein the top portion includes a fastening system for securing the medical device inside the protective cushion, the first and second side portions cooperatively forming the fastening system, the first side portion being shaped such that the opening is wider at a proximal end adjacent to the bottom portion and narrower at a distal end away from the bottom portion wherein, when the medical device is inserted into the opening, the narrower distal end of the opening prevents the medical device from falling out of the opening; and wherein the bottom portion is made of a soft material.

9. The protective cushion of claim 8, wherein the top portion is also made of the soft material.

10. The protective cushion of claim 8, wherein the top portion has a tapered shape that is wider at a proximal end adjacent to the bottom portion and narrower at a distal end away from the bottom portion.

11. The protective cushion of claim 8, wherein the first and second side portions cooperatively form the fastening system for securing the medical device in the protective cushion.

12. The protective cushion of claim 11, wherein the opening separating the first and second side portions is wider at a proximal end adjacent to the bottom portion and narrower at a distal end away from the bottom portion, such that, when the medical device is inserted into the opening, the narrower distal end helps prevent the medical device from falling out of the opening separating the first and second side portions.

13. The protective cushion of claim 8, wherein the opening separating the first and second side portions comprises a lower generally circular section at a proximal end adjacent to the bottom portion of the protective cushion and a slit section connected to the lower generally circular section and extending away from the bottom portion, the lower generally circular section having a diameter and the slit section having a width, the diameter of the lower generally circular section being greater than the width of the slit section.

14. The protective cushion of claim 8, wherein the narrower central portion of the first side portion includes a central longitudinal protrusion for receiving at least a portion of the medical device.

15. A protective cushion for preventing a medical device from damaging the skin of a patient, the protective cushion comprising:

a flexible single piece made of a soft material, the flexible single piece comprising:

a bottom portion for resting against the skin of the patient and separating the medical device from the skin of the patient; and a top portion having an opening shaped for receiving the medical device, the opening extending across the length of the top portion and separating a first side portion from a second side portion, wherein the first side portion comprises a narrower central portion and two wider peripheral portions on opposite ends of the narrower central portion making the opening wider adjacent to the narrower central portion and making the opening narrower adjacent to the wider peripheral portions;

wherein the top portion includes a fastening system for securing the medical device in the protective cushion, the first and second side portions cooperatively forming the fastening system; and wherein the opening separating the first and second side portions comprises a lower generally circular section at a proximal end adjacent to the bottom portion of the protective cushion and a slit section connected to the lower generally circular section and extending away from the bottom portion, the lower generally circular section having a diameter and the slit section having a width, the diameter of the lower generally circular section being greater than the width of the slit section.

\* \* \* \* \*